(12) United States Patent
Yip et al.

(10) Patent No.: US 11,504,194 B2
(45) Date of Patent: Nov. 22, 2022

(54) SYSTEM AND METHOD FOR ROBUST AND LOW-COST MULTI-AXIS FORCE SENSOR

(71) Applicant: THE REGENTS OF THE UNIVERSITY OF CALIFORNIA, Oakland, CA (US)

(72) Inventors: Michael Yip, La Jolla, CA (US); Jun Zhang, La Jolla, CA (US); Alex Tran, La Jolla, CA (US); Winnie Kuang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 732 days.

(21) Appl. No.: 16/468,804

(22) PCT Filed: Dec. 13, 2017

(86) PCT No.: PCT/US2017/066123
§ 371 (c)(1),
(2) Date: Jun. 12, 2019

(87) PCT Pub. No.: WO2018/112041
PCT Pub. Date: Jun. 21, 2018

(65) Prior Publication Data
US 2020/0093560 A1    Mar. 26, 2020

Related U.S. Application Data

(60) Provisional application No. 62/433,578, filed on Dec. 13, 2016.

(51) Int. Cl.
*G01L 1/00* (2006.01)
*A61B 34/30* (2016.01)
(Continued)

(52) U.S. Cl.
CPC .............. *A61B 34/30* (2016.02); *A61B 34/76* (2016.02); *A61B 90/06* (2016.02); *G01L 1/005* (2013.01);
(Continued)

(58) Field of Classification Search
CPC . G01L 1/005; G01L 5/16; G01P 15/18; A61B 34/30; A61B 34/76; A61B 90/06
See application file for complete search history.

(56) References Cited

U.S. PATENT DOCUMENTS

| 4,951,510 A | 8/1990 | Holm | |
| 7,107,825 B2 * | 9/2006 | Degertekin | G01N 29/2456 73/105 |

(Continued)

*Primary Examiner* — Bryan Bui
(74) *Attorney, Agent, or Firm* — Stuart H. Mayer; Mayer & Williams PC

(57) ABSTRACT

Systems and methods according to present principles provide for three axis force sensing in a convenient and manufacturable way. In one implementation, a vibrating motor is attached at the fixed end of an anisotropic structure, such as a rod, which then vibrates in a circular motion. A monitor such as a 3-axis accelerometer is also attached to the anisotropic structure. The resulting motion is then mapped electronically for analysis. With no force applied, a circular motion is achieved. When a net force is applied to the free, vibrating end of the rod, the circular pattern which is traced out becomes distorted, e.g., progressively flattened into an ellipse, in a repeatable way which is directly proportional to the applied force. The axis of the applied force can be ascertained according to the direction in which the ellipse forms. Systems and methods according to present principles may be used in any application in which force sensing is needed, e.g., robotics, including robotic surgery.

18 Claims, 12 Drawing Sheets

(51) Int. Cl.
  *A61B 34/00* (2016.01)
  *A61B 90/00* (2016.01)
  *G01L 5/16* (2020.01)
  *G01P 15/18* (2013.01)

(52) U.S. Cl.
  CPC .............. *G01L 5/16* (2013.01); *G01P 15/18* (2013.01); *A61B 2090/064* (2016.02); *A61B 2562/0219* (2013.01)

(56) References Cited

U.S. PATENT DOCUMENTS

| | | | |
|---|---|---|---|
| 7,555,398 B2 * | 6/2009 | Fowler | G01C 17/00 702/151 |
| 7,712,366 B2 | 5/2010 | Beyeler | |
| 2004/0020279 A1 | 2/2004 | Degertekin | |
| 2007/0151390 A1 | 7/2007 | Blumenkranz | |
| 2008/0151441 A1 | 6/2008 | Freitag | |
| 2016/0308420 A1 | 10/2016 | Harrison | |

* cited by examiner

SYSTEM AND METHOD FOR ROBUST AND LOW-COST MULTI-AXIS FORCE SENSOR

CROSS-REFERENCE TO RELATED APPLICATIONS

This application is a National Phase of PCT/US2017/066123, filed Dec. 13, 2017, which claims benefit of priority to U.S. Provisional Patent Application Ser. No. 62/433,578, filed Dec. 13, 2016, entitled "SYSTEM AND METHOD FOR ROBUST AND LOW-COST MULTI-AXIS FORCE SENSOR", owned by the assignee of the present application and herein incorporated by reference in its entirety.

FIELD

The invention relates to force sensors.

BACKGROUND

It is known in the field of force sensing to apply resonance as a means of measuring an applied force. However, in these uses, the force sensitivity has been in a single axis, e.g., a scale for weight, a diaphragm for pressure, or the like.

In the area of teleoperated surgical systems, current force sensing methods for involve integrated force sensors that are difficult to miniaturize, nonsterilizable, nonversatile, delicate, and costly. Such force sensing methods include use of displacement sensors and resistive sensors. Displacement sensors detect the displacement of an elastic material such as a linear spring. Resistive sensors use strain gauges, which are bonded to the structure, to make force measurements: when force is applied to the structure, there is strain, thereby causing the electrical resistance in the strain gauge to change. By measuring the resistance and change in resistance, the applied force can be estimated.

However, neither of these methods is adaptable to multi-axis force instruments as in robotic surgery. Moreover, these methods often involve a tradeoff between functionality in measuring the magnitude and direction of force, and its cost in manufacturing, as systems involving these methods are typically composed of delicate and complex parts.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Systems and methods according to present principles meet the needs of the above in several ways, and in particular provides for a multi-axis force sensor in a single, simple device. Systems and methods may be especially employed in a force sensor for any structure that has an anisotropic moment of inertia, where the moment of inertia of one axis of the structure is greater than that of another axis.

In one embodiment, by attaching a vibrating motor at the fixed end of an anisotropic structure such as a rod, the free end of the rod vibrates in a pattern, e.g., circular motion. By also attaching a monitor such as a 3-axis accelerometer to the rod, the circular motion can be mapped electronically for analysis. Then, by applying a force to the free, vibrating end of the rod, the pattern is modified, e.g., the circular pattern which is traced out becomes distorted, e.g., progressively flattened into an ellipse, in a repeatable way which is directly proportional to the applied force. Further, the axis of the applied force can be ascertained according to the direction in which the pattern is modified, e.g., in the direction in which the ellipse forms, e.g., up-to-down, left-to-right, diagonally, and so on. Lastly, the exact direction of the applied force is determined according to the shift of the center of the ellipse versus the position of the unperturbed original circular resonance pattern.

In one aspect, the invention is directed towards a method of providing multiple axis force sensing, comprising: providing a motor coupled to an anisotropic structure, the anisotropic structure further coupled to a force sensor; operating the motor to cause the anisotropic structure to continuously move such that a portion of the anisotropic structure coupled to the force sensor traces out a first path in space; receiving at the anisotropic structure an applied force; monitoring a second path traced by the portion of the anisotropic structure in response to the applied force; and calculating an applied force based on the monitored first path and second path.

Implementations of the invention may include one or more of the following. The motor may cause the distal tip of the anisotropic structure to revolve or precess. The motor may act on the anisotropic structure with a vibrating force. The motor may include a rotating or revolving eccentric or off-center weight. The receiving at the anisotropic structure an applied force includes receiving at the distal tip of the anisotropic structure the applied force. The calculating an applied force based on the monitored first path and second path includes calculating an applied force based on a change between the monitored first path and second path. The force sensor may be an accelerometer coupled to the anisotropic structure.

In another aspect, the invention is directed towards a force sensing device using a three axis accelerometer, which forms a portion of a multiple axis force sensor, including: a multiple axis force sensor, comprising: a sensor, the sensor including a anisotropic structure with a distal tip; a motor coupled to the sensor; a monitor to measure movement of the anisotropic structure upon operation of the motor; and a computing environment configured to receive data from the monitor and calculate an applied force applied to the sensor based on the received data.

Implementations of the invention may include one or more of the following.

The motor may be configured to cause the distal tip of the anisotropic structure to revolve or precess. The motor may be configured to act on the anisotropic structure with a vibrating force. The motor may include a rotating or revolving eccentric or off-center weight. The computing environment may calculate the applied force based on the measured movement of the anisotropic structure. The monitor may include a force sensor. The force sensor may include an accelerometer coupled to the anisotropic structure. The accelerometer may be a multi axis accelerometer, or a three axis accelerometer. The sensor may be an anisotropic structure.

Advantages of the invention may include, in certain embodiments, one or more of the following. Systems and methods according to present principles provide a convenient and manufacturable design for a multi-axis, e.g., three axis, force sensor. Such sensors according to present principles can be attached to any tool head the user, e.g., doctor, desires. Such sensors are generally orders of magnitude less expensive than other force sensors. The systems and methods provide a low cost solution to measure force, which is convenient to implement, and useful in a variety of areas. Other advantages will be understood from the description that follows, including the figures and claims.

This Summary is provided to introduce a selection of concepts in a simplified form. The concepts are further described in the Detailed Description section. Elements or steps other than those described in this Summary are possible, and no element or step is necessarily required. This Summary is not intended to identify key features or essential features of the claimed subject matter, nor is it intended for use as an aid in determining the scope of the claimed subject matter. The claimed subject matter is not limited to implementations that solve any or all disadvantages noted in any part of this disclosure.

BRIEF DESCRIPTION OF THE DRAWINGS

Like reference numerals refer to like elements throughout. Elements are not to scale unless otherwise noted.

DETAILED DESCRIPTION

An exemplary implementation is described below, in the context of force sensing for haptic feedback in surgical systems. However, it will be understood that systems and methods according to present principles may be employed in any number of applications where force sensing is performed. In addition, while systems and methods shown here indicate how a pattern that is a circle is modified into a pattern that is an ellipse, such is due to the geometry of the system. Other patterns, and pattern modifications, will also be understood to be encompassed within the scope.

In this context it is noted that most existing surgical robotic arms do not feature any force sensing at all. The few that do feature a force feedback sensor have disadvantages. In particular, one problem with existing force sensing techniques is the level of complexity of the parts. For example, strain gauge force sensors are composed of extremely small and precisely machined metal parts that are prohibitively expensive to use. These sensors also restrict the types of tools that can be used on surgical robotic arms, due in particular to space and geometry impedance caused by the sensor.

Vibration Force Sensors according to present principles provide force sensing to the surgeon when the same is, e.g., operating on teleoperated surgical systems during minimally invasive surgery. This feedback includes the magnitude and direction of force applied onto the end effector of the instrument. With such systems, the surgeon can be better aware of the interactive forces between the surgical tool and the patient's tissues and organs, thereby improving the safety and accuracy of the surgery.

The vibration force sensor, according to present principles, provides information of the magnitude and direction of force applied onto the end effector of an anisotropic structure. In the context of robotic surgery, this information is crucial for surgeons operating surgical robotic systems to gain an accurate measurement of the forces involved during operation. Other types of applications will also be understood.

As indicated above, in one implementation of present principles, systems and methods according to present principles are constructed by attaching a vibrating motor at the fixed end of a rod, which then vibrates in a circular motion. It will be understood that the vibrating motor may be disposed in a number of locations relative to the rod, so long as the vibratory motion is transmitted to the rod or other sensor component A monitor such as a 3-axis accelerometer is also attached to the rod. The resulting motion can then be mapped electronically for analysis.

Figure 7:
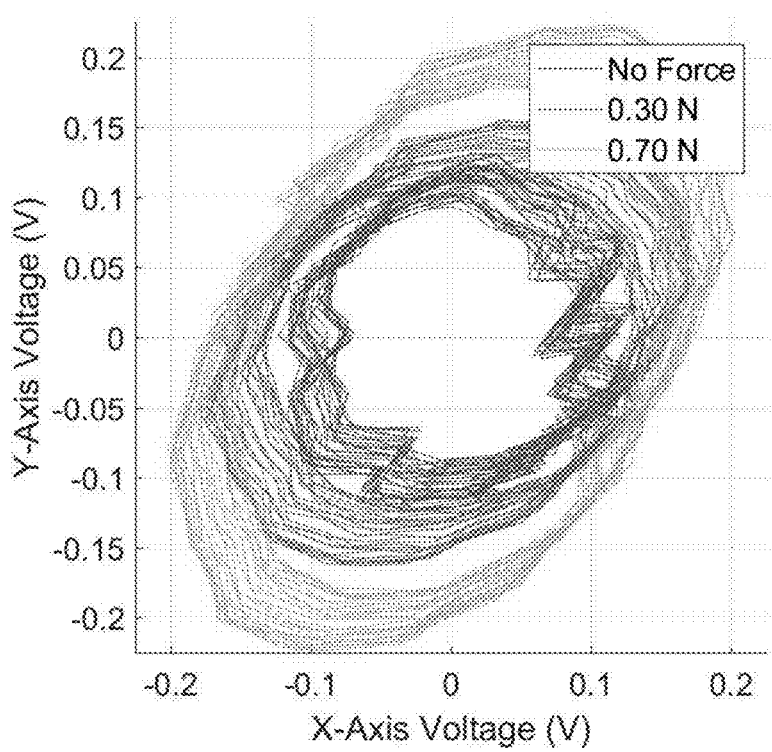
FIG. 7 is a chart developed using a system according to present principles, showing the raw acceleration profiles resulting from different magnitudes of axial forces applied onto the tip of the structure, in the same direction. The small ellipse is with no force, the next largest is with 0.30 N force, and the largest with 0.7N force.
Figure 9:
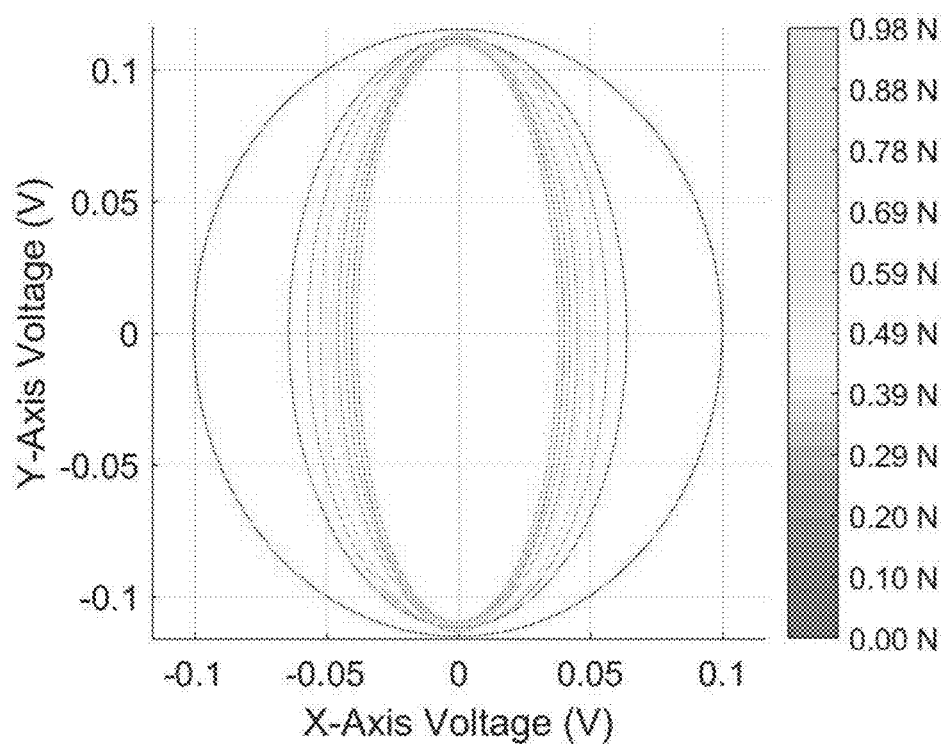
FIG. 9 shows overlapped fitting of acceleration profiles for transverse forces applied in one specified direction for various magnitudes, showing that, with increasing force, the pattern's shape becomes biased (e.g., ellipse becomes narrowed) with increasing force along a certain axis.

With no force applied, a circular motion is achieved. This may be seen in FIGS. 7 and 9.

When a net force is applied to the free, vibrating end of the rod, the circular pattern which is traced out becomes distorted, e.g., progressively flattened into an ellipse, in a repeatable way which is directly proportional to the applied force. The axis of the applied force can be ascertained according to the direction in which the ellipse forms, e.g., up-to-down, left-to-right, diagonally, and so on, as indicated in the attached figures. The exact direction of the applied force is determined according to the shift of the center of the ellipse versus the position of the unperturbed original circular resonance pattern (or the center thereof).

In more detail, a vibration force sensor according to present principles generally works by mechanically exciting the robotic arm (simplified in this experiment as a cantilevered beam but any rod or sensor will do, and the same generally include some sort of distal tip where forces are received, although the same may be received at any location on the rod) with an eccentric rotating mass (ERM) motor. This causes the beam to vibrate in a circular motion. The rotational vibration is measured by a high resolution (5000 samples/s) accelerometer capable of tracking the rotation profile of the robotic arm at 180 Hz. When a device having such a beam is placed at the end effector (or other location) of a robotic device, e.g., the endowrist, and contacts tissue within the body, the vibration is damped along the axis of contact, causing the motion of the beam to become skewed in the direction of contact. As contact force increases, the vibration is increasingly damped. This causes the ellipsoid path of the beam to become narrower.

To quantify the effect, the parameters of the ellipse can be characterized, e.g., the ellipse rotation and size, by determining the ellipse shape and rotation using a model of the ellipse shape with no force applied, and then transforming this model of the ellipse to match with the ellipse shape produced from directional forces, and performing additional regression analysis to find additional models corresponding to the forces.

Figure 1:
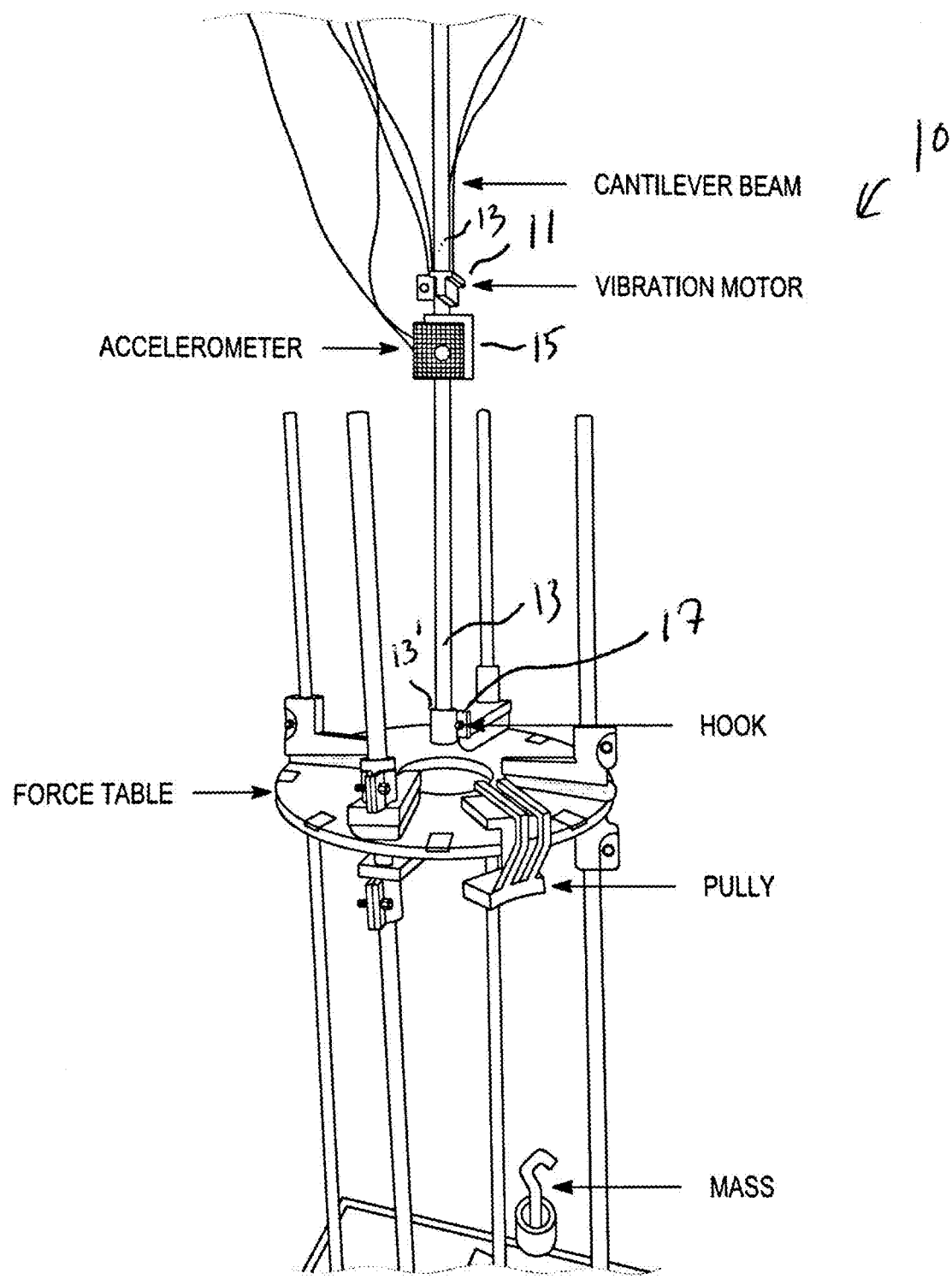
FIG. 1 shows an image of an exemplary experimental set up configuration of the three axis force sensor for exerting forces on the transverse plane.

For example, and referring to the system 10 of FIG. 1, one system and method according to present principles includes a motor 11 coupled to an anisotropic structure 13, the anisotropic structure further coupled to a force sensor 15. Various types of motors are described below. The anisotropic structure 13 can include a rod or cantilever beam or the like, and the same generally operate as a force sensor tip. The force sensor 15 may include an accelerometer such as a three axis accelerometer.

As described, the motor causes the anisotropic structure to continuously move such that a portion of the anisotropic structure coupled to the force sensor traces out a first path in space. When an applied force is received at the anisotropic structure, the first path or pattern is modified. By monitoring the modified or a second path traced by the portion of the anisotropic structure in response to the applied force; an applied force may be calculated based on the monitored first path and second path.

In experiments, the responses of the vibrating beam motion from an applied directional force have been monitored. Equipment used to generate and acquire this data include a solid aluminum beam, a force table, masses, a ERM vibration motor (Precision MicroDrives, 303 103), a triple axis accelerometer (Sparkfun, ADXL 337), and a multifunction DAQ (National Instruments, USB6000).

Figure 4:
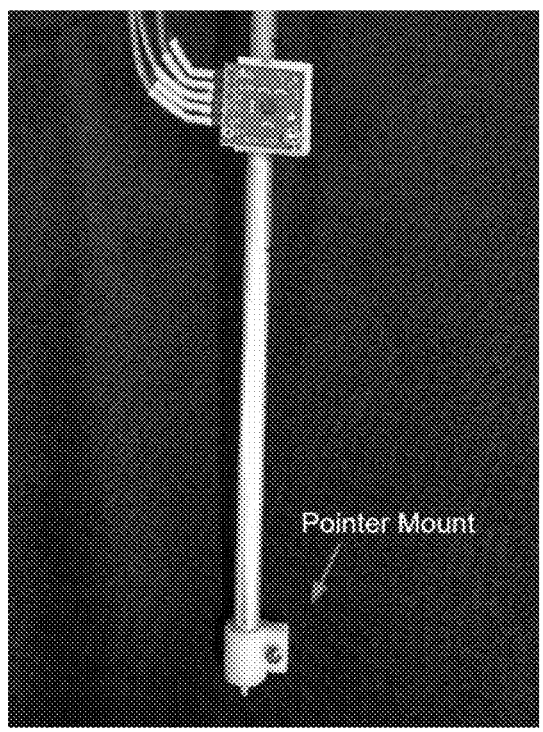
FIG. 4 shows a close view of an exemplary experimental set up of a pointer mount attached to the end of a rod which was used to exert forces along the axial plane.

The vibration motor and the triple axis accelerometer were attached, in close proximity to each other, onto the vertically mounted beam. The triple axis accelerometer was positioned so that the z-axis lined along the transverse beam, and the x axis and y axes were on the plane perpendicular to the transverse beam. A hook mount 17 was attached onto the tip of the vertically mounted beam 13 to exert transverse forces onto the tip 13' of the beam (see FIG. 1). A pointer mount was attached onto the tip of the vertically mounted beam to exert axial forces onto the tip of the beam (see also FIG. 4).

Figure 2:
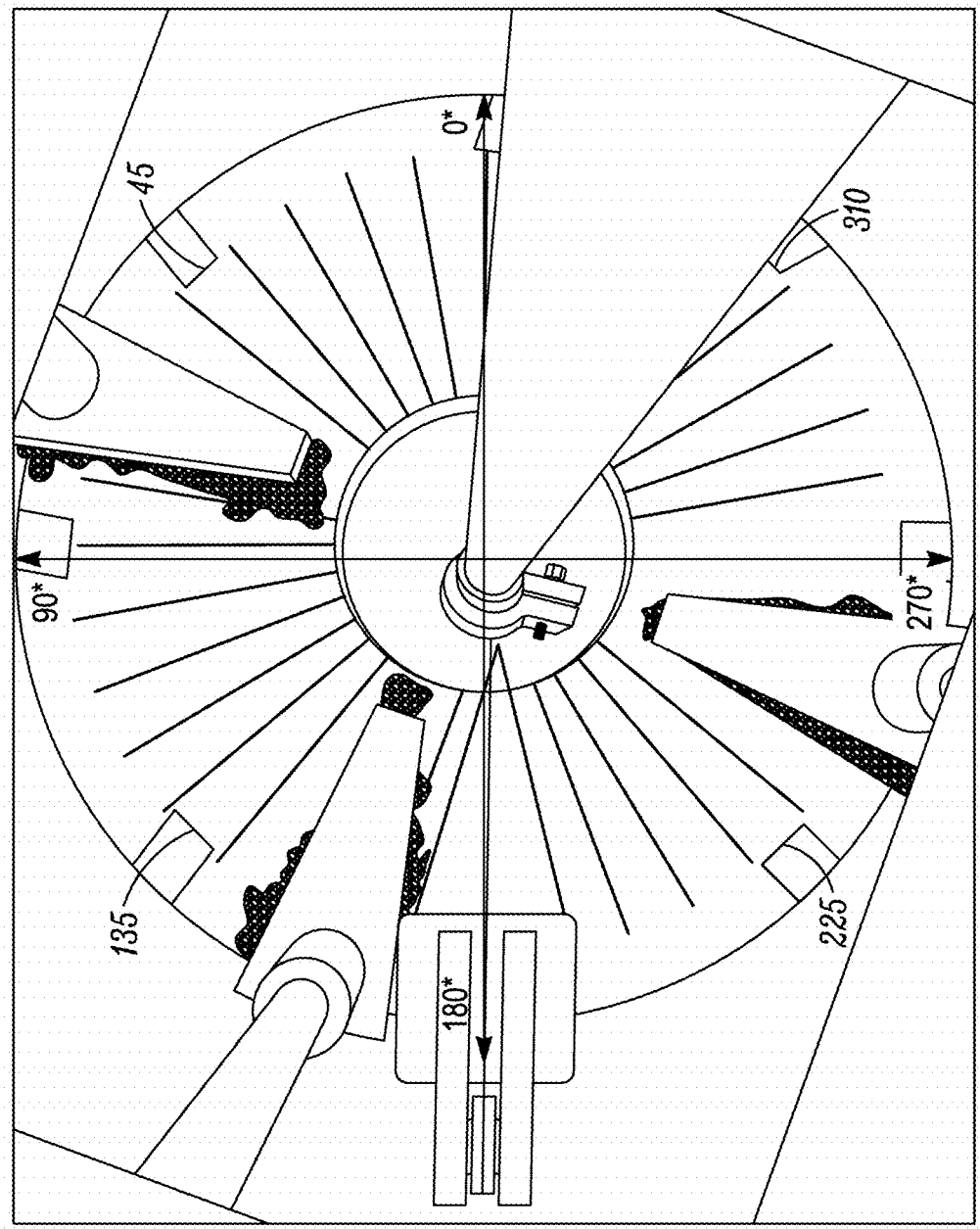
FIG. 2 shows a top-down image of the configuration of FIG. 1, indicating potential directions of force.
Figure 3:
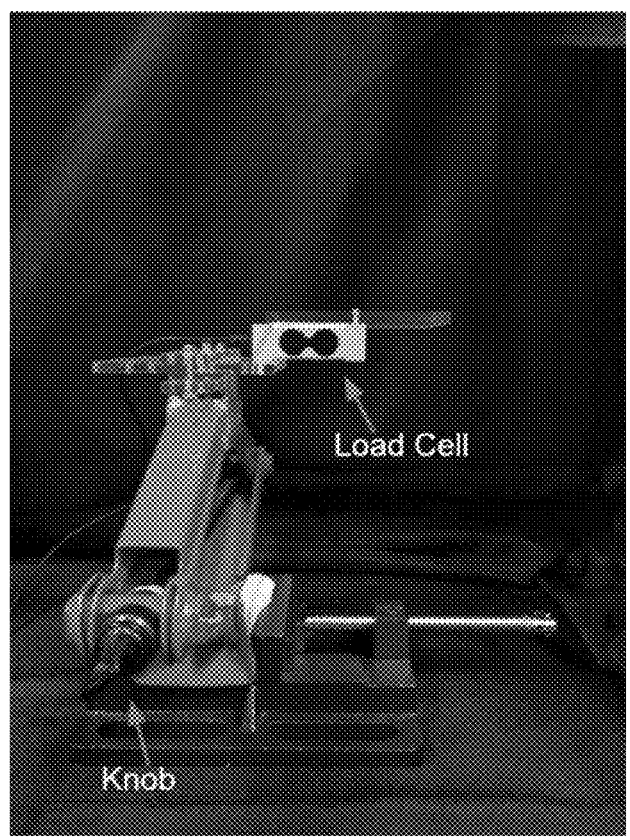
FIG. 3 shows an image of an exemplary experimental set up configuration which includes a lift platform used to exert forces along the axial plane.

Experimental data was obtained by collecting analog voltage measurements from the triple axis accelerometer, while the beam was in constant vibration, in each of the following procedures. Data was collected using the multifunction DAQ and LABVIEW at a rate of 5,000 Hz. First, data was recorded without any force applied to the tip of the beam. Data was then recorded while a constant force was applied to the tip of the beam. Next, the magnitude of the force applied onto the tip of the beam was increased. This process was repeated again, but with force applied in a different direction. The directions of forces tested were along the transverse plane and axial plane of the structure. Directional forces tested on the transverse plane were applied via the force table (see FIG. 1 and FIG. 2). This type of force ranged in the directions of 0 degrees to 170 degrees in increments of 10 degrees (see FIG. 2). Forces tests on the axial plane of the structure were applied via the lift platform (see FIG. 3). The magnitudes of forces tested in both planes ranged from no force up to 1 Newton. The clear relationship between the magnitude and direction of applied force, and the acceleration profile of the beam has been found. This relationship can thus be used to estimate the magnitude and direction of force. After data was gathered for all sets of directional force, the data was processed using MATLAB. As previously stated, the x-axis and y-axis were along the transverse plane of the beam. Forces applied in the directions 0 degrees and 90 degrees corresponded to the +x axis and +y axis respectively (see FIG. 2).

Figure 5:
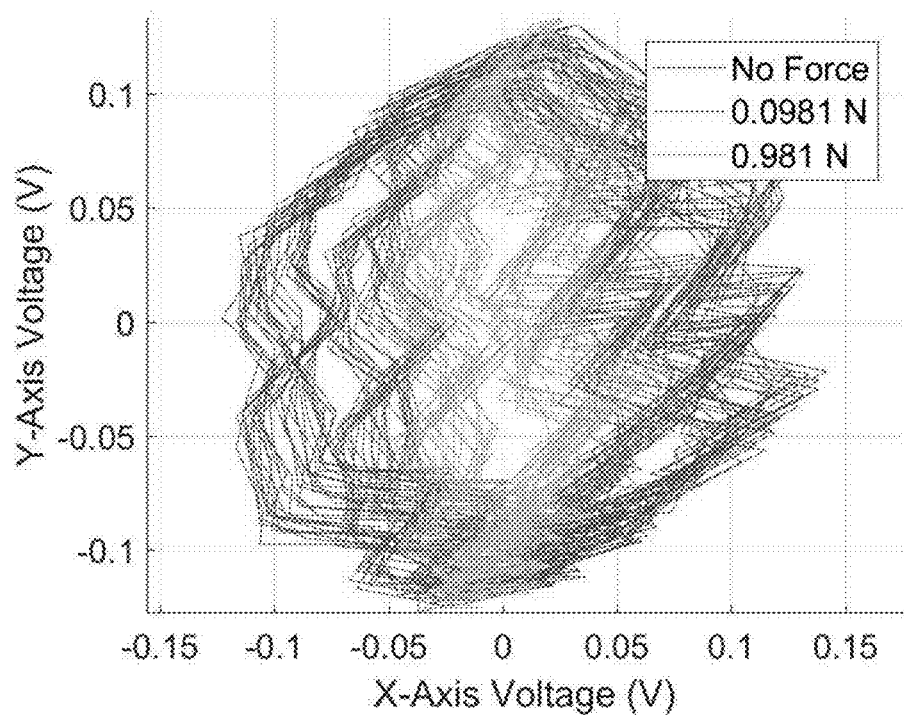
FIG. 5 is a chart developed using a system according to present principles, showing a raw acceleration profile plot for a transverse force resulting from different magnitudes of transverse forces applied in the same direction onto the tip of the structure. The innermost and thus narrowest generally-ellipse-shaped pattern represents 0.981 N, the next narrowest is 0.0981 N, and the widest, which is more of a circular pattern, is with no force.
Figure 6:
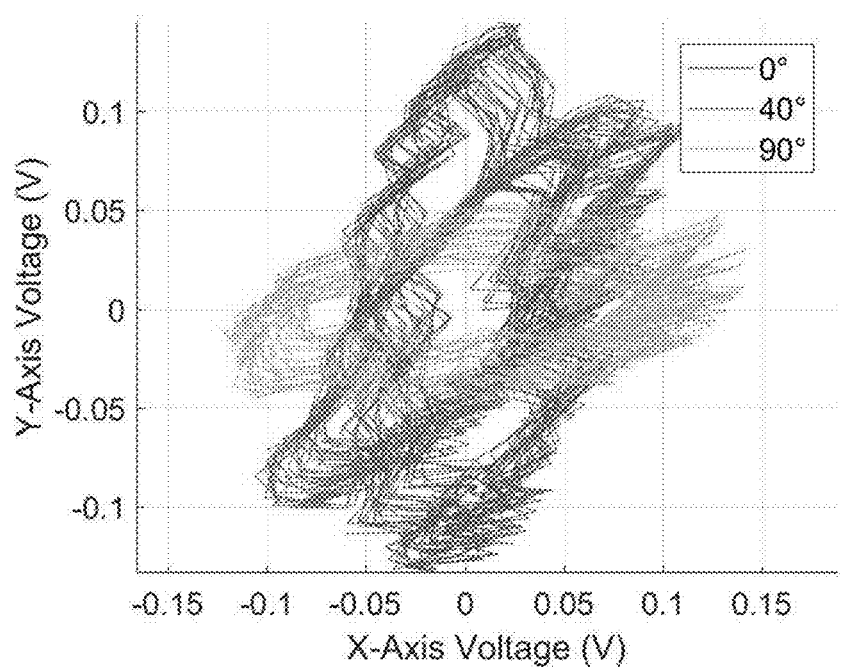
FIG. 6 is a raw acceleration profile plot for transverse force showing varying direction of applied force. As may be seen, different directions of force change the orientation of the "ellipse". In this example, the most nearly horizontal ellipse is the case with 90° force, the next is with 40° force, and the most vertical is with 0° force.

Plots of raw voltage data from the accelerometer from the y-axis versus the x-axis indicate that when force is applied to the tip of the vibrating beam, the resulting acceleration profile is resembled by an ellipse shape. Increasing the magnitude of force applied onto the tip of the beam along the transverse plane results in an ellipse with a decreasing length in the semi-minor axis (see FIG. 5). Changing the direction of force applied onto the tip of the beam along the transverse plane results in an ellipse with a different orientation (see FIG. 6). When an increasing magnitude of force is applied along the axial plane of the beam, both the semi-minor and semi-major axis of the ellipse increases (see FIG. 7).

Figure 8:
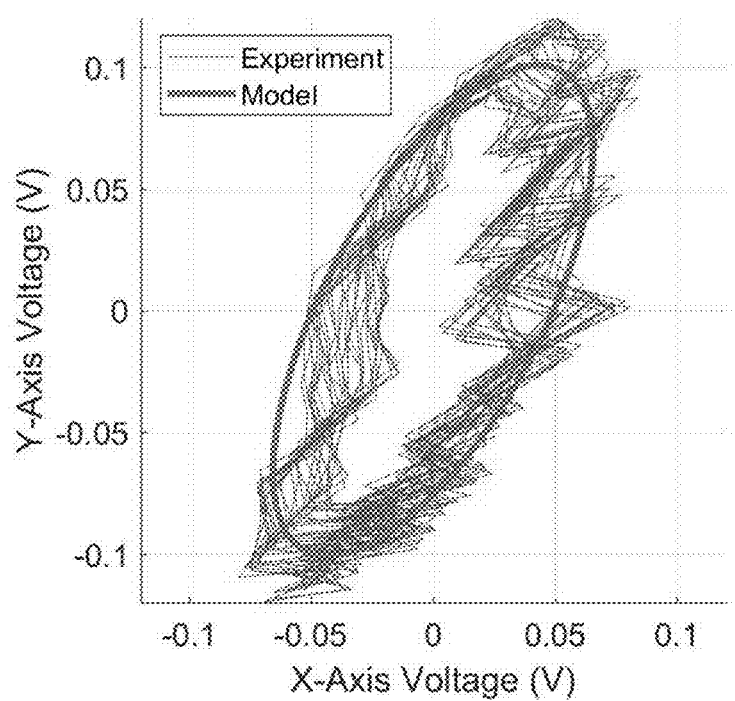
FIG. 8 shows a fitted acceleration profile onto a raw acceleration profile with transverse force being applied, with the ellipse representing the model and the other pattern data representing the experiment.
Figure 10:
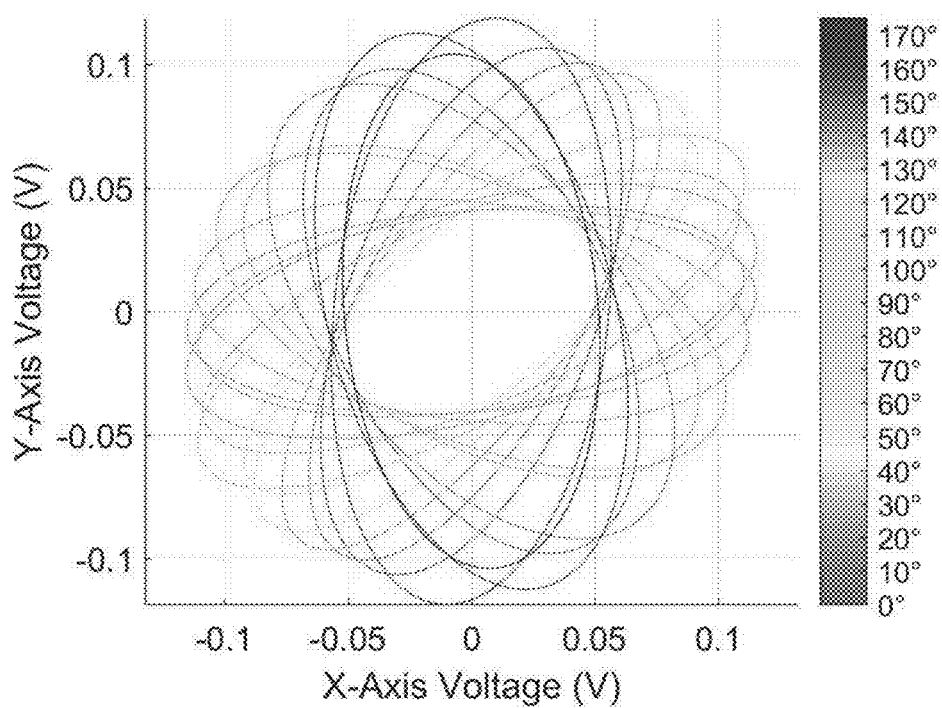
FIG. 10 shows overlapped fitting of acceleration profiles for transverse forces applied with one specified magnitude for all directions, showing that the pattern which characterizes the acceleration profile has a particular orientation with different forces applied. The plot shows transverse forces with the same magnitude, applied in different directions in the range of 0° to 170°. The most horizontal is with about a 90° force, and the most vertical is that with the more extreme ends, e.g., 0° or 170-180°.
Figure 11:
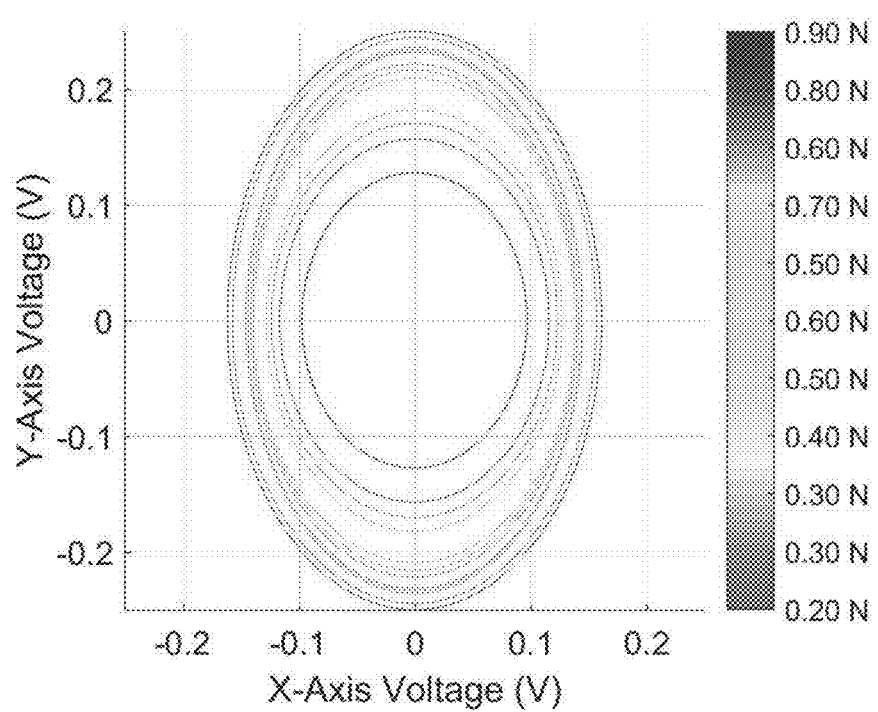
FIG. 11 shows fitted acceleration profiles of axial forces applied with increasing magnitudes. The smallest ellipse is with the minimum of force, while the largest is with the largest force.
Figure 12:
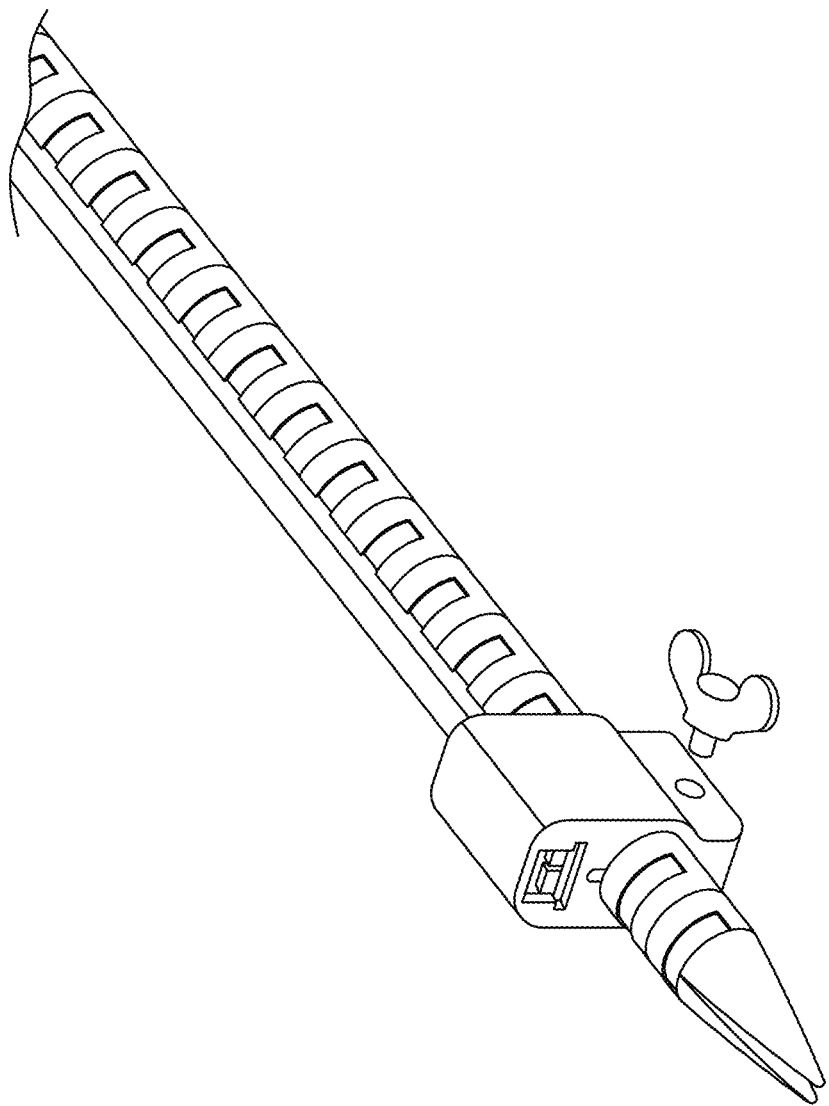
FIG. 12 is an image of an exemplary force tip sensor.

After fitting these raw acceleration profiles to a model (FIG. 8), the correction between the magnitude of forces applied and the resulting changes in the length of the axes of the ellipse was developed. According to these results, increasing the magnitude of forces applied along the transverse plane decreases the semi-minor axis length of the ellipse (see FIG. 9), while the semi-major axis length of the ellipse does not change. Increasing the magnitude of forces applied along the axial plane increases both the semi-major axis length and the semi-minor axis length of the ellipse (see FIG. 11). Changing the direction of force applied along the transverse plane will only influence the orientation of the ellipse (see FIG. 10).

While the above force sensing systems and methods are initially studied and targeted for estimating force between a surgical robotic arm and tissues within the body, the same can also be used as a force sensor for any structure that has an anisotropic moment of inertia, where the moment of inertia of one axis of the structure is greater than that of another axis.

Exemplary applications include robotics, robotic surgery (including among others laparoscopic surgery), haptics, sensory applications, and so on.

While the invention herein disclosed is capable of obtaining the objects hereinbefore stated, it is to be understood that this disclosure is merely illustrative of the presently preferred embodiments of the invention and that no limitations are intended other than as described in the appended claims.

The invention claimed is:

1. A method of providing multiple axis force sensing, comprising:
   a. providing a motor coupled to an anisotropic structure, the anisotropic structure further coupled to a force sensor;
   b. operating the motor to cause the anisotropic structure to continuously move such that a portion of the anisotropic structure coupled to the force sensor traces out a first path in space;
   c. receiving at the anisotropic structure an applied force;
   d. monitoring a second path traced by the portion of the anisotropic structure in response to the applied force; and
   e. calculating an applied force based on the monitored first path and second path.

2. The method of claim 1, wherein the motor causes the distal tip of the anisotropic structure to revolve or precess.

3. The method of claim 2, wherein the motor acts on the anisotropic structure with a vibrating force.

4. The method of claim 2, wherein the motor includes a rotating or revolving eccentric or off-center weight.

5. The method of claim 1, wherein the receiving at the anisotropic structure an applied force includes receiving at the distal tip of the anisotropic structure the applied force.

6. The method of claim 1, wherein the calculating an applied force based on the monitored first path and second path includes calculating an applied force based on a change between the monitored first path and second path.

7. The method of claim 1, wherein the force sensor is an accelerometer coupled to the anisotropic structure.

8. The method of claim 7, wherein the accelerometer is a multi axis accelerometer.

9. The method of claim 8, wherein the accelerometer is a three axis accelerometer.

10. A multiple axis force sensor, comprising:
    a. a sensor, the sensor including a anisotropic structure with a distal tip;
    b. a motor coupled to the sensor, wherein the motor is configured to cause the distal tip of the anisotropic structure to revolve or precess;
    c. a monitor to measure movement of the anisotropic structure upon operation of the motor; and
    d. a computing environment configured to receive data from the monitor and calculate an applied force applied to the sensor based on the received data.

11. The multiple axis force sensor of claim 10, wherein the sensor is an anisotropic structure.

12. The multiple axis force sensor of claim 10, wherein the motor is configured to act on the anisotropic structure with a vibrating force.

13. The multiple axis force sensor of claim 10, wherein the motor includes a rotating or revolving eccentric or off-center weight.

14. The multiple axis force sensor of claim 10, wherein the computing environment is configured to calculate the applied force based on the measured movement of the anisotropic structure.

15. The multiple axis force sensor of claim 10, wherein the monitor includes a force sensor.

16. The multiple axis force sensor of claim 15, wherein the force sensor is an accelerometer coupled to the anisotropic structure.

17. The multiple axis force sensor of claim 16, wherein the accelerometer is a multi axis accelerometer.

18. The multiple axis force sensor of claim 17, wherein the accelerometer is a three axis accelerometer.

* * * * *